US012102361B2

(12) United States Patent
Aebi et al.

(10) Patent No.: US 12,102,361 B2
(45) Date of Patent: Oct. 1, 2024

(54) BONE PLATES HAVING MULTI-USE SCREW HOLES FOR LOCKING AND COMPRESSION SCREWS, AND RELATED SYSTEMS AND METHODS

(71) Applicant: DePuy Synthes Products, Inc., Raynham, MA (US)

(72) Inventors: This Aebi, Grenchen (CH); Mirko Rocci, Bettlach (CH); Joel Oberli, Niederdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/508,037

(22) Filed: Oct. 22, 2021

(65) Prior Publication Data

US 2022/0133370 A1  May 5, 2022

Related U.S. Application Data

(60) Provisional application No. 63/107,699, filed on Oct. 30, 2020.

(51) Int. Cl.
  *A61B 17/80* (2006.01)
  *A61B 17/88* (2006.01)
  *A61B 17/56* (2006.01)

(52) U.S. Cl.
  CPC ...... *A61B 17/8014* (2013.01); *A61B 17/8057* (2013.01); *A61B 17/88* (2013.01); *A61B 2017/564* (2013.01)

(58) Field of Classification Search
  CPC ... A61B 17/56; A61B 2017/564; A61B 17/80; A61B 17/8004; A61B 17/8014; A61B 17/8052; A61B 17/8057; A61B 17/88
  See application file for complete search history.

(56) References Cited

U.S. PATENT DOCUMENTS

| | | |
|---|---|---|
| 6,669,701 B2 | 12/2003 | Steiner et al. |
| 6,719,759 B2 | 4/2004 | Wagner et al. |

(Continued)

FOREIGN PATENT DOCUMENTS

| | | |
|---|---|---|
| AU | 2011200981 A1 | 9/2011 |
| CN | 101703420 A | 5/2010 |

(Continued)

OTHER PUBLICATIONS

U.S. Appl. No. 63/107,699, filed Oct. 30, 2020 entitled Bone Plates Having Multi-Use Screw Holes for Locking and Compression Screws, and Related Systems and Methods.

(Continued)

*Primary Examiner* — Larry E Waggle, Jr.
(74) *Attorney, Agent, or Firm* — BakerHostetler

(57) ABSTRACT

A bone plate has an outer surface, a bone-facing surface opposite the outer surface, and an interior surface that defines a hole extending from the outer surface to the bone-facing surface along a central hole axis. The interior surface further defines a ramp that extends from the outer surface toward the bone-facing surface and plate threads that extend from the ramp toward the bone-facing surface and are configured for optional locking engagement with external threads on a first head of a locking bone fixation member. The interior surface further defines a contact profile in a reference plane that extends along the central hole axis. The contact profile is defined at least by the ramp and is spaced from the central hole axis in an offset direction perpendicular to the central hole axis. The contact profile is configured to translate the bone plate in the offset direction responsive to contact with an exterior surface of a second head of a compression bone fixation member as the second head advances within the hole along an insertion axis that is offset from the central hole axis in the offset direction.

18 Claims, 10 Drawing Sheets

(56) References Cited

U.S. PATENT DOCUMENTS

| | | | |
|---|---|---|---|
| 6,730,091 B1 * | 5/2004 | Pfefferle | A61B 17/863 606/291 |
| 7,354,441 B2 | 4/2008 | Frigg | |
| 7,695,502 B2 | 4/2010 | Orbay et al. | |
| 7,776,076 B2 | 8/2010 | Grady et al. | |
| 7,951,176 B2 | 5/2011 | Grady et al. | |
| 7,976,570 B2 | 7/2011 | Wagner et al. | |
| 8,343,196 B2 | 1/2013 | Schneider | |
| 8,758,346 B2 | 6/2014 | Koay et al. | |
| 8,845,698 B2 | 9/2014 | Schneider | |
| 8,852,245 B2 | 10/2014 | Schneider | |
| 8,876,873 B2 | 11/2014 | Schneider | |
| 8,940,029 B2 | 1/2015 | Leung et al. | |
| 9,107,711 B2 | 8/2015 | Hainard | |
| 9,161,791 B2 | 10/2015 | Frigg | |
| 9,295,505 B2 | 3/2016 | Schneider | |
| 9,308,034 B2 | 4/2016 | Grady et al. | |
| 9,314,284 B2 | 4/2016 | Chan et al. | |
| 9,931,148 B2 | 4/2018 | Grady et al. | |
| 10,231,768 B2 | 3/2019 | Grady et al. | |
| 10,342,586 B2 | 7/2019 | Schneider | |
| 10,653,466 B2 | 5/2020 | Grady et al. | |
| 10,772,665 B2 | 9/2020 | Bosshard et al. | |
| 2004/0049196 A1 | 3/2004 | Jackson | |
| 2008/0161860 A1 | 7/2008 | Ahrens et al. | |
| 2009/0312803 A1 | 12/2009 | Austin et al. | |
| 2012/0264528 A1 | 10/2012 | Isobe et al. | |
| 2012/0265255 A1 | 10/2012 | Hilse et al. | |
| 2014/0018862 A1 | 1/2014 | Koay et al. | |
| 2014/0207194 A1 | 7/2014 | Wolter | |
| 2014/0316473 A1 | 10/2014 | Pfeiffer et al. | |
| 2016/0367299 A1 | 12/2016 | Paolino et al. | |
| 2018/0003212 A1 * | 1/2018 | Seo | F16B 33/02 |
| 2018/0064477 A1 | 3/2018 | Lopez et al. | |
| 2018/0132913 A1 | 5/2018 | Davison et al. | |
| 2018/0161081 A1 | 6/2018 | Anding et al. | |
| 2018/0250043 A1 | 9/2018 | Rapalo et al. | |
| 2018/0310972 A1 | 11/2018 | Anding et al. | |
| 2019/0269444 A1 | 9/2019 | Schneider | |
| 2019/0328430 A1 * | 10/2019 | Bosshard | A61B 17/8057 |
| 2020/0237420 A1 | 7/2020 | Grady et al. | |
| 2020/0390483 A1 | 12/2020 | Oberli et al. | |
| 2021/0015526 A1 | 1/2021 | Oberli et al. | |

FOREIGN PATENT DOCUMENTS

| | | | | |
|---|---|---|---|---|
| CN | 201861741 U | | 6/2011 | |
| CN | 102188282 A | | 9/2011 | |
| CN | 103961173 A | | 8/2014 | |
| CN | 105232131 A | | 1/2016 | |
| DE | 102015102629 A1 | * | 10/2016 | A61B 17/8014 |
| DE | 102015102629 | * | 12/2022 | |
| EP | 2919688 A1 | | 9/2015 | |
| JP | 2006-511252 A | | 4/2006 | |
| JP | 2010-536427 A | | 12/2010 | |
| WO | 2006/014436 A1 | | 2/2006 | |
| WO | 2011/078365 A1 | | 6/2011 | |
| WO | 2013/036362 A1 | | 3/2013 | |
| WO | 2014/078289 A1 | | 5/2014 | |
| WO | 2019/211681 A1 | | 11/2019 | |
| WO | 2020/234669 A1 | | 11/2020 | |
| WO | 2020/250052 A1 | | 12/2020 | |

OTHER PUBLICATIONS

"General Administration of Quality Supervision, Inspection and Quarantine of the People's Republic of China", National Standard of the People's Republic of China GB/T 192-2003, No. 192-2003 Edition, May 22, 2023, pp. 423-424.

* cited by examiner

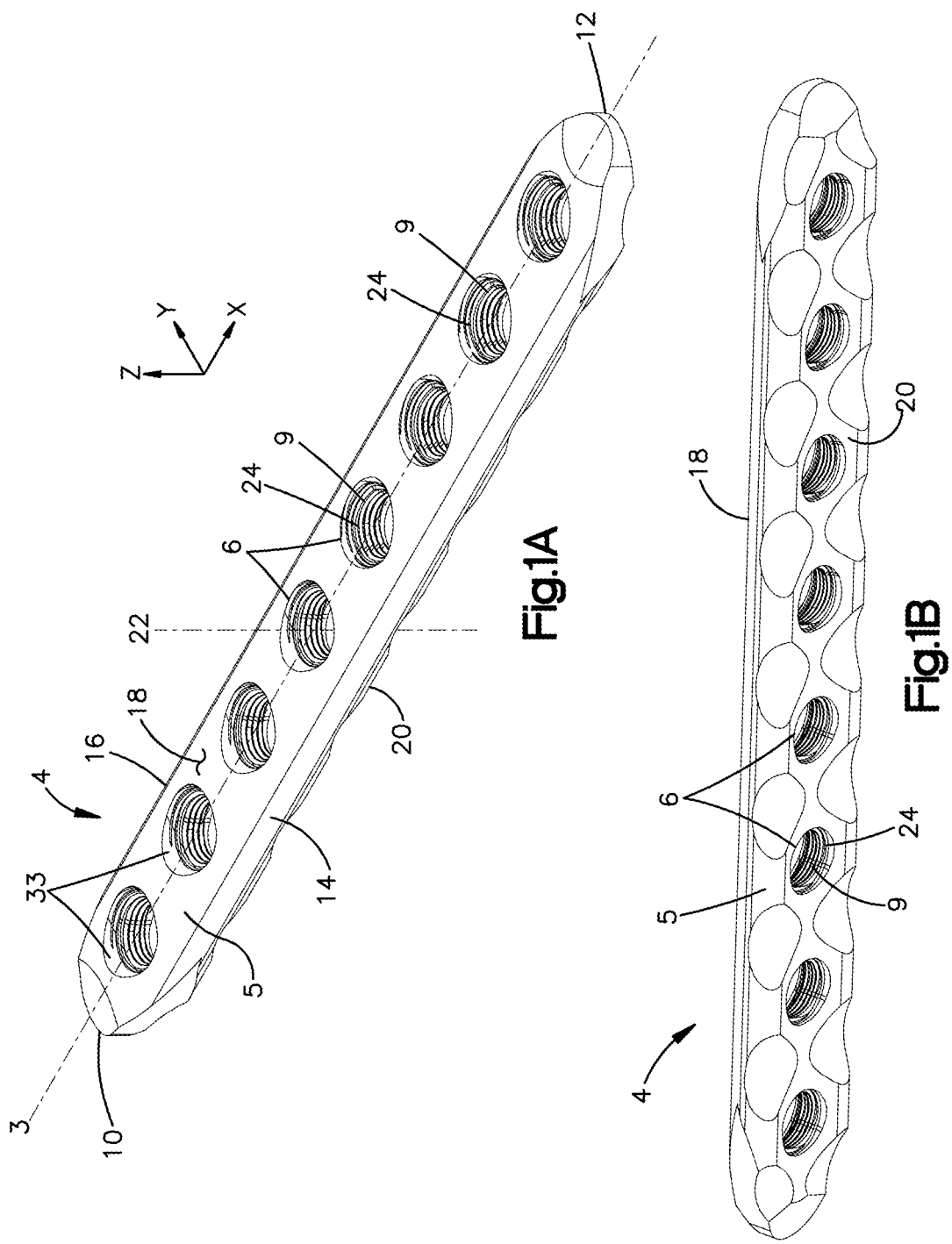

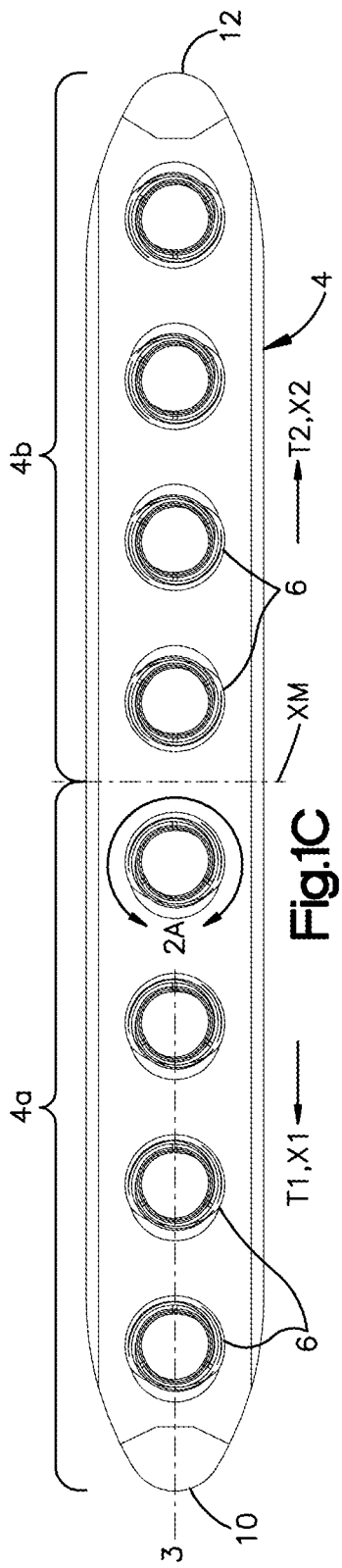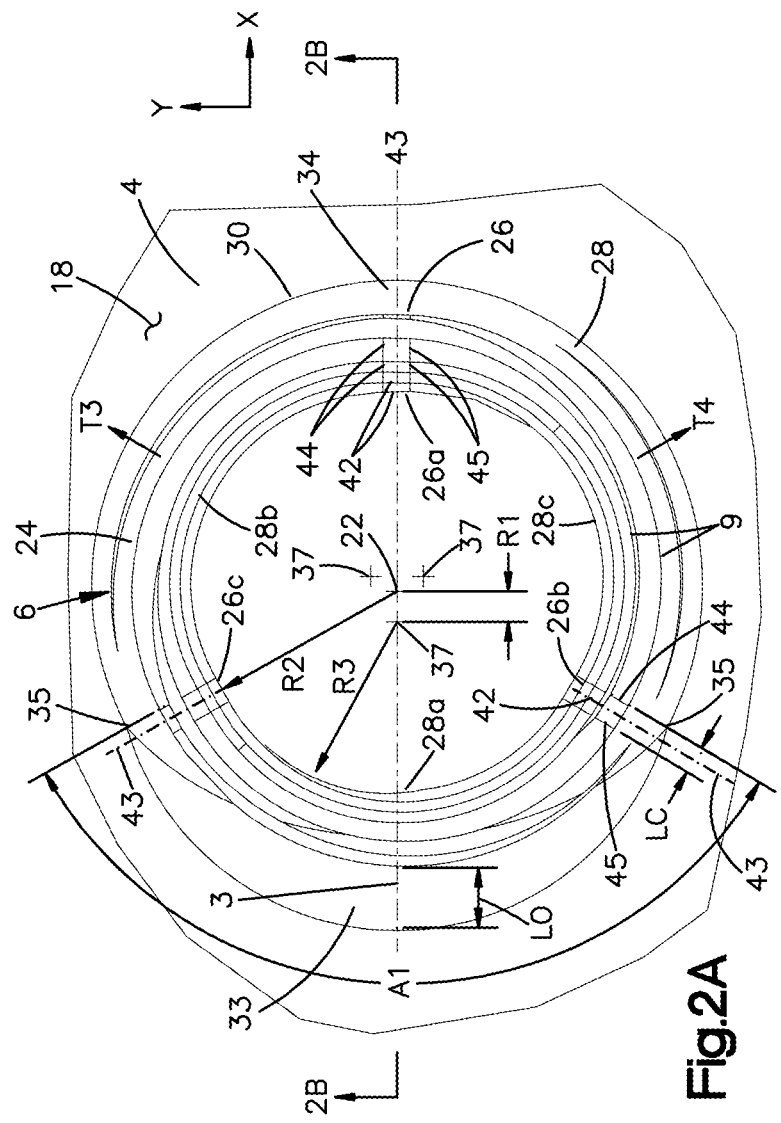

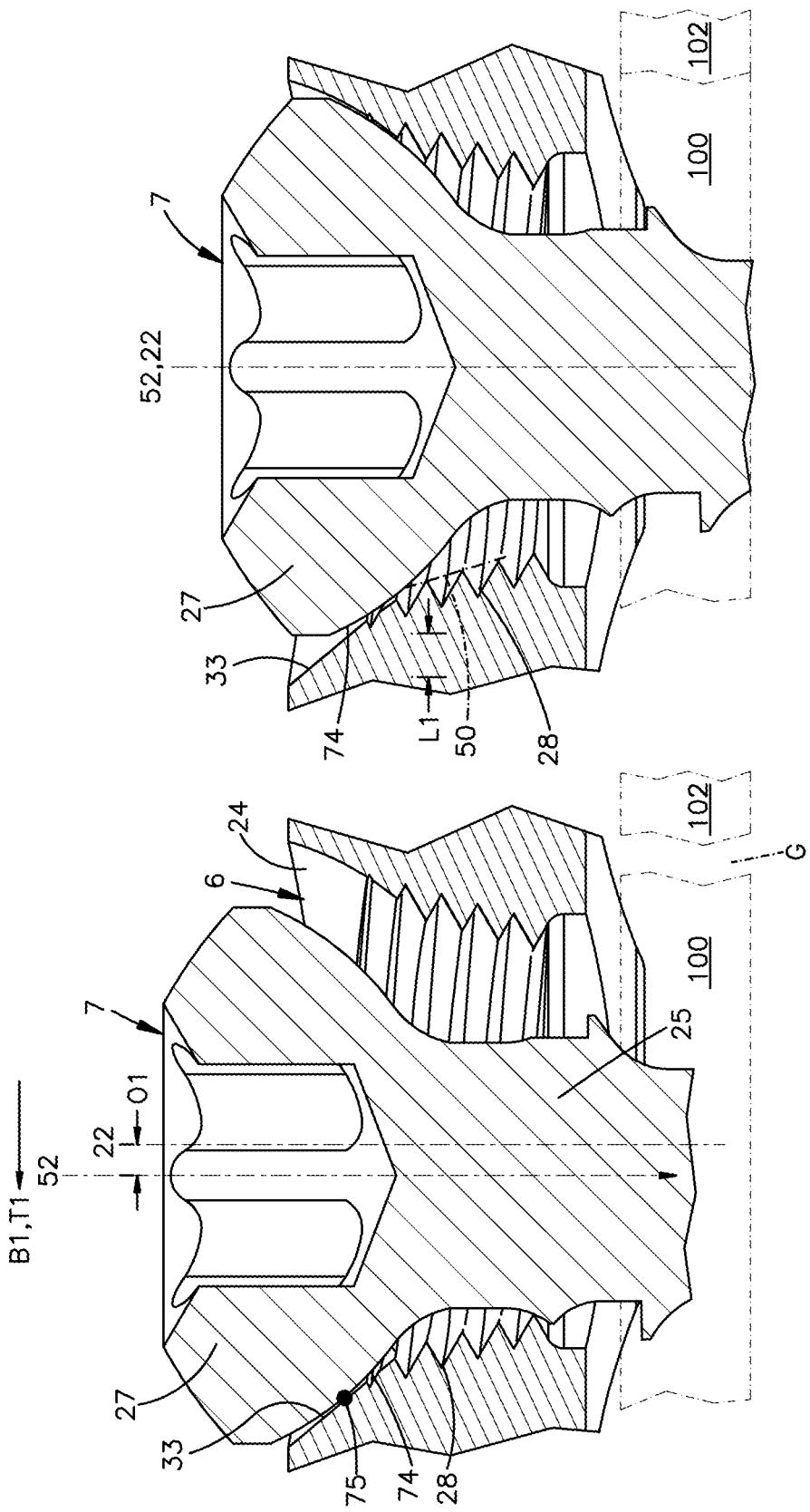

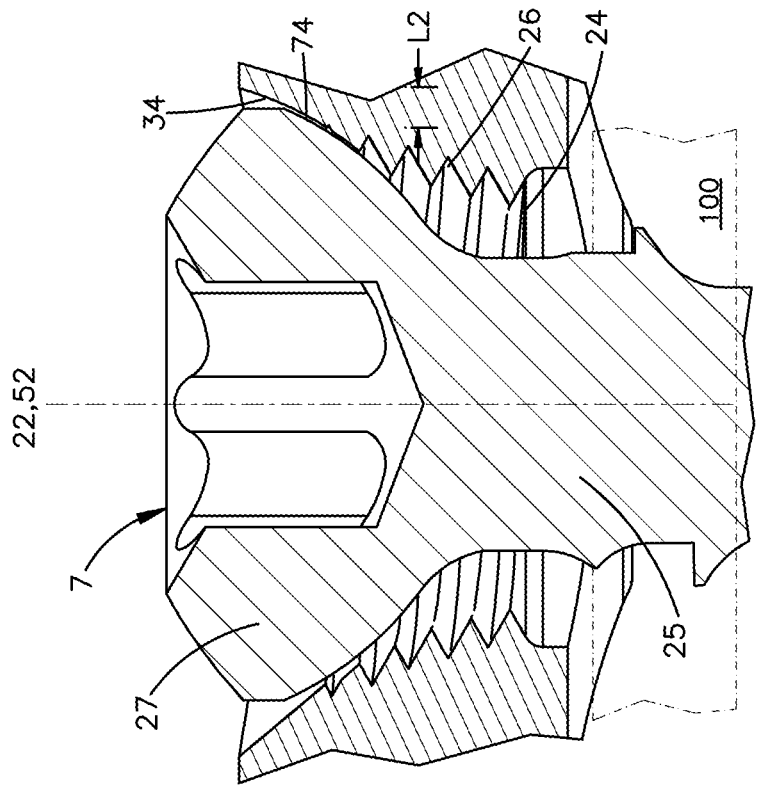
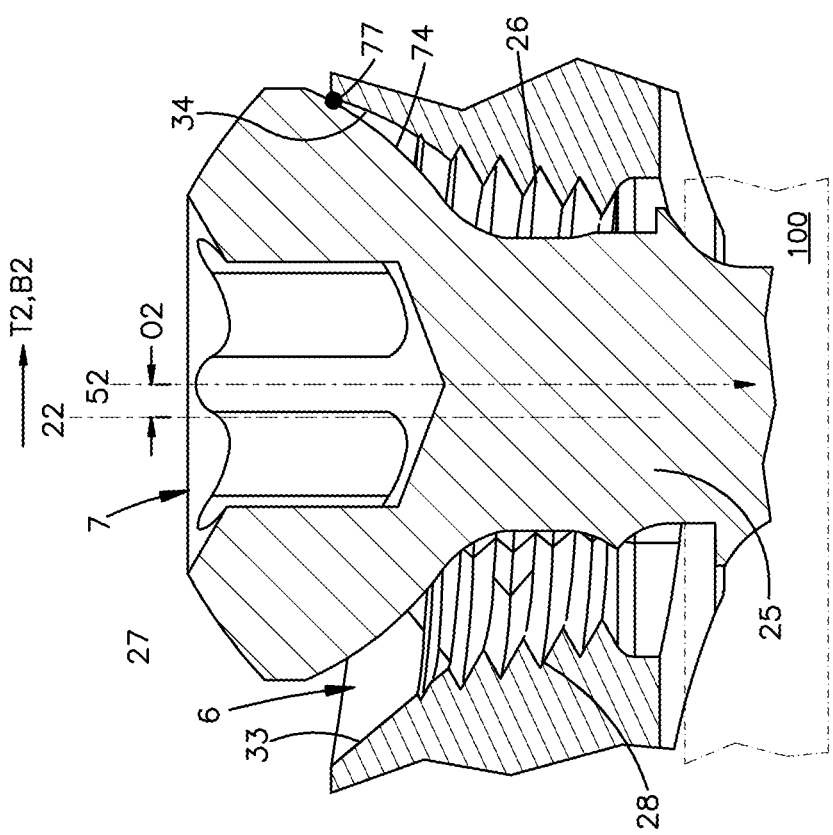

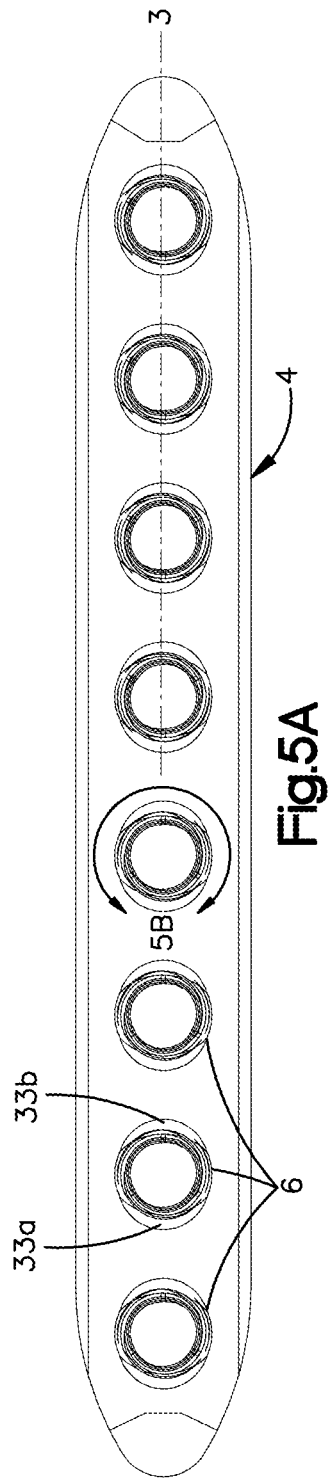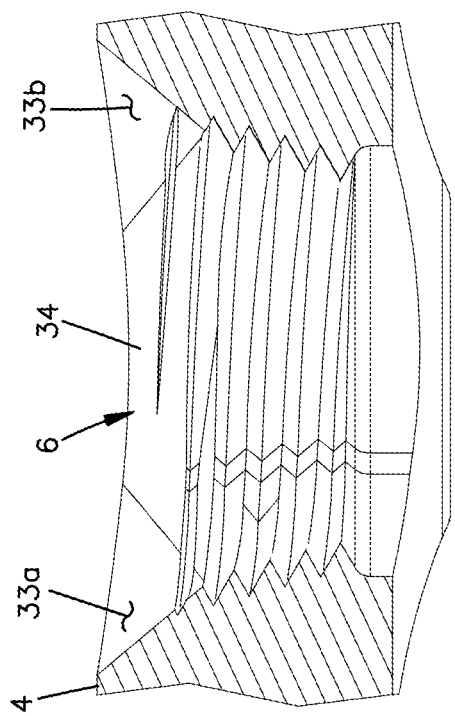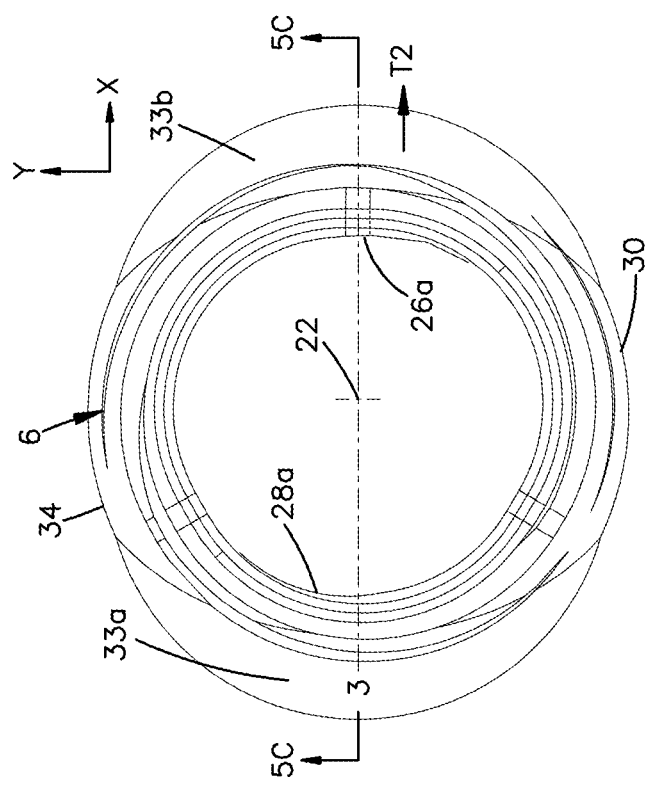

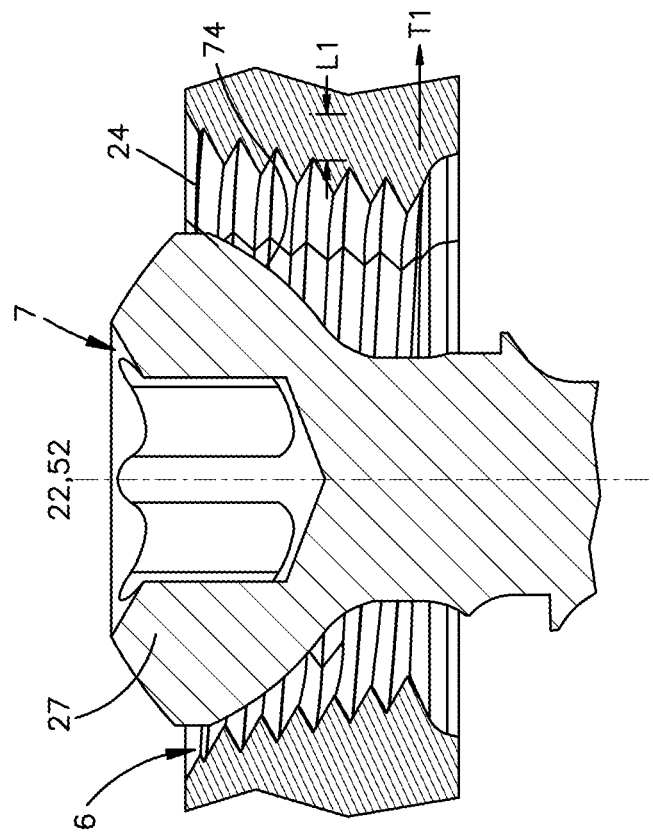
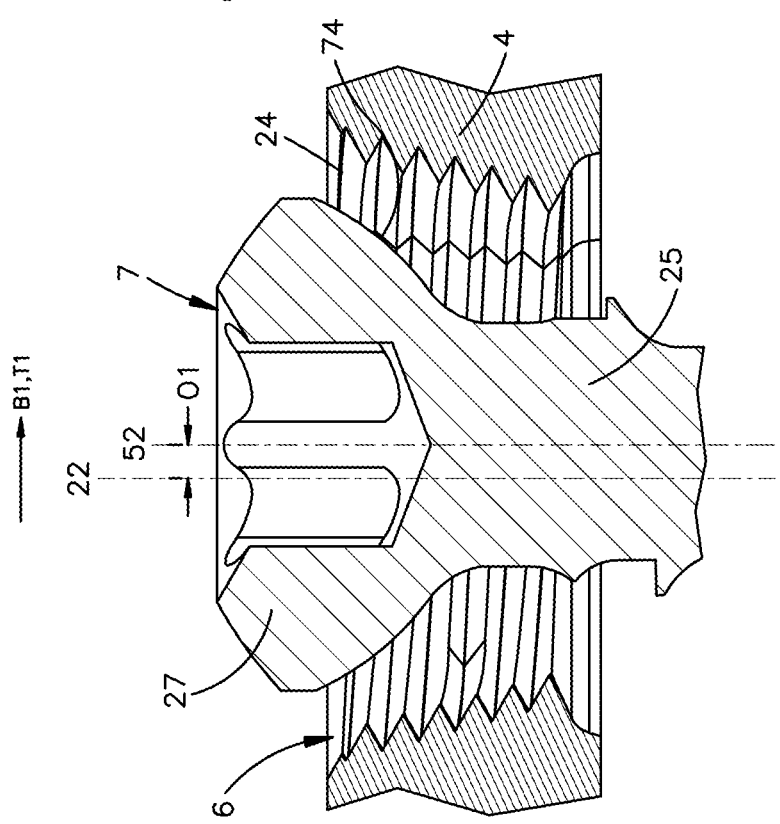

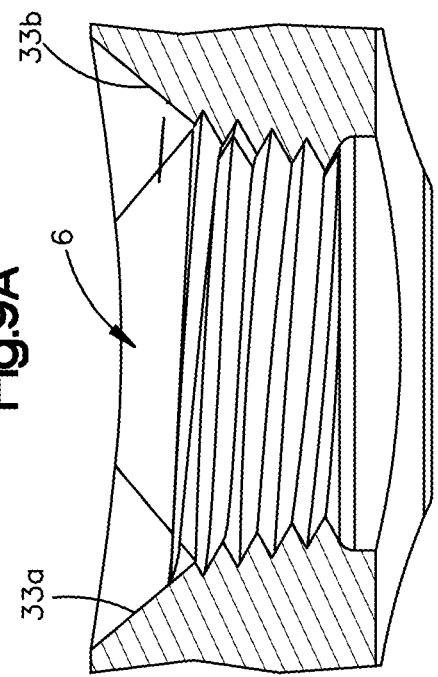
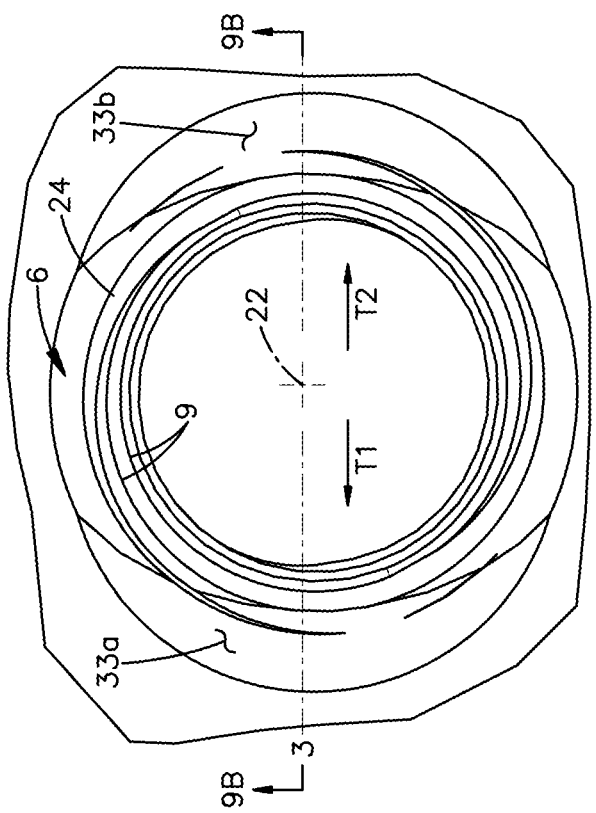
Fig.9A / Fig.9B
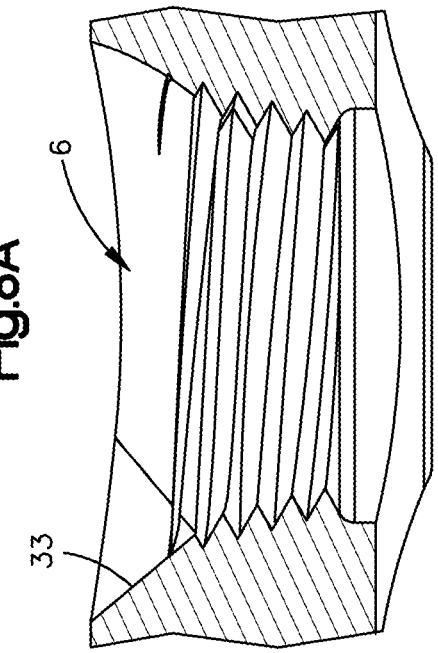
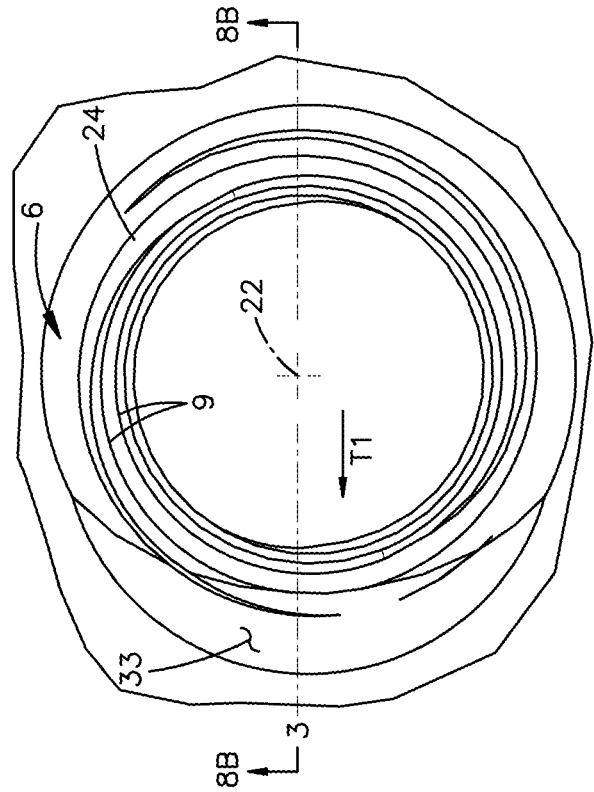
Fig.8A / Fig.8B

BONE PLATES HAVING MULTI-USE SCREW HOLES FOR LOCKING AND COMPRESSION SCREWS, AND RELATED SYSTEMS AND METHODS

CROSS REFERENCE TO RELATED APPLICATIONS

This application claims the benefit under 35 U.S.C. § 119(e) of U.S. Provisional Patent Application No. 63/107,699, filed Oct. 30, 2020, in the name of Aebi et al., the entire contents of which are hereby incorporated by reference.

TECHNICAL FIELD

The present invention relates to bone plates for receiving bone anchors to affix the bone plates to bone, and particularly relates to bone plates having threaded fixation holes that are configured for multiple uses, particularly for selective threaded locking with a threaded head of a locking bone anchor or for dynamic compression via sliding engagement with a head of a compression bone anchor.

BACKGROUND

Bone plate systems for the internal fixation of bone fractures are well known. Conventional bone plate systems are particularly well-suited to promote the healing of a fracture. A bone anchor, such as a bone screw, is inserted through a fixation aperture or hole in a bone plate and is threaded into bone to compress, neutralize, buttress, tension, band, and/or bridge the fracture ends together. Bone screws that are capable of locking with the bone plate can be employed to transfer loads from one fractured bone part, over a plate, and onto another fractured bone part without drawing the bone against the plate, and to avoid loosening or backing out the bone screws with respect to the plate (which can lead to poor alignment and poor clinical results). One known embodiment of such a screw employs a screw head with external threads for engaging with a corresponding thread on the inner surface of a fixation hole, which are hereinafter referred to as "locking holes", to lock the screw to the plate. These screws, which are hereinafter referred to as "locking screws", can include standard-type locking screws that are configured to lock within a fixation hole substantially only at a "nominal" orientation whereby the central screw axis is substantially aligned with the central hole axis, as well as "variable-angle" (VA) locking screws that are configured to lock within a fixation hole at either a nominal orientation or an "angulated" orientation whereby the central screw axis is oriented at an acute angle with respect to the respective central hole axis.

Bone plate systems can also be adapted to provide anatomical reduction between fractured bone parts. The bone plates of such systems include one or more holes having ramp geometries that engage a smooth exterior surface of a screw head of a "compression screw" in a manner causing dynamic compression, meaning that the bone plate translates with respect to the compression screw and underlying bone along a direction generally perpendicular to the screw axis of the compression screw. Such holes are hereinafter referred to as "compression holes". Bone plates can include both locking holes and compression holes. For example, one or more of the locking holes can be employed to receive a locking screw that affixes the bone plate to a first underlying bone segment. One or more of the compression holes can then be employed to receive a compression screw that drives into a second underlying bone segment and effectively pushes, via engagement between the head of the compression screw and the ramp geometry within the hole, the bone plate in a translation direction that reduces a gap between the first and second underlying bone segments.

SUMMARY

According to an embodiment of the present disclosure, a bone plate has an outer surface, a bone-facing surface opposite the outer surface, and an interior surface that defines a hole extending from the outer surface to the bone-facing surface along a central hole axis. The interior surface further defines a ramp that extends from the outer surface toward the bone-facing surface and plate threads that extend from the ramp toward the bone-facing surface and are configured for optional locking engagement with external threads on a first head of a locking bone fixation member. The interior surface further defines a contact profile in a reference plane that extends along the central hole axis. The contact profile is defined at least by the ramp and is spaced from the central hole axis in an offset direction perpendicular to the central hole axis. The contact profile is configured to translate the bone plate in the offset direction responsive to contact with an exterior surface of a second head of a compression bone fixation member as the second head advances within the hole along an insertion axis that is offset from the central hole axis in the offset direction.

According to another embodiment of the present disclosure, a method of seating a bone screw in a hole defined by an interior surface of a bone plate includes inserting a shaft of the bone screw through the hole at an offset distance, measured between a central axis of the bone screw and a central axis of the hole along a first direction that is perpendicular to the central axis of the hole, and into underlying bone. The method includes contacting an outer surface of the head of the bone screw against at least one ramp surface defined by the interior surface within the hole. The interior surface includes internal threads that extend between the at least one ramp surface and the underlying bone. The method further includes driving the bone screw, during the contacting step, toward the underlying bone along the central axis of the screw, thereby translating the bone plate in the first direction relative to the bone screw.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings:

FIG. 1A is a perspective view showing a top of a bone plate having multi-use anchor holes, according to an embodiment of the present disclosure;

FIG. 1B is a perspective view showing a bottom of a bone plate illustrated in FIG. 1A;

FIG. 1C is a top view of the bone plate illustrated in FIG. 1A;

FIG. 2A is an enlarged top view of a multi-use anchor hole shown in area 2A-2A of FIG. 1C;

FIG. 3A is the sectional side view of the multi-use anchor hole of FIG. 2B showing a compression screw inserted eccentrically therein at a first position, according to an embodiment of the present disclosure;

FIG. 3B is the sectional side view of the multi-use anchor hole of FIG. 2B showing the compression screw inserted eccentrically therein at a fully seated position;

FIG. 4A is the sectional side view of the multi-use anchor hole of FIG. 2B showing a compression screw inserted eccentrically therein at a third position opposite the first position shown in FIG. 3A, according to an embodiment of the present disclosure;

FIG. 4B is the sectional side view of the multi-use anchor hole of FIG. 2B showing the compression screw inserted therein at a fully seated position;

FIG. 5A is a top view of a bone plate having multi-use anchor holes, according to another embodiment of the present disclosure;

FIG. 5B is an enlarged top view of a multi-use anchor hole shown in area 5B-5B of FIG. 5A;

FIG. 5C is a sectional side view of the multi-use anchor hole taken along section line 5C-5C of FIG. 5B;

FIG. 6C is a sectional side view of the elongated multi-use anchor hole taken along section line 6C-6C of FIG. 6B, showing a compression screw inserted eccentrically within the hole at a first position, according to an embodiment of the present disclosure;

FIG. 6D is a sectional side view of the elongated multi-anchor hole of FIG. 6C, showing the compression screw inserted therein at a fully seated position;

FIG. 8A is a top view of a multi-use anchor hole having a circular hole profile, according to a further embodiment of the present disclosure;

FIG. 8B is a sectional side view of the multi-use anchor hole taken along section line 8B-8B of FIG. 8A;

FIG. 9A is a top view of a multi-use anchor hole having a circular hole profile, according to an additional embodiment of the present disclosure; and FIG. 9B is a sectional side view of the multi-use anchor hole taken along section line 9B-9B of FIG. 9A.

DETAILED DESCRIPTION OF ILLUSTRATIVE EMBODIMENTS

Figure 2B:
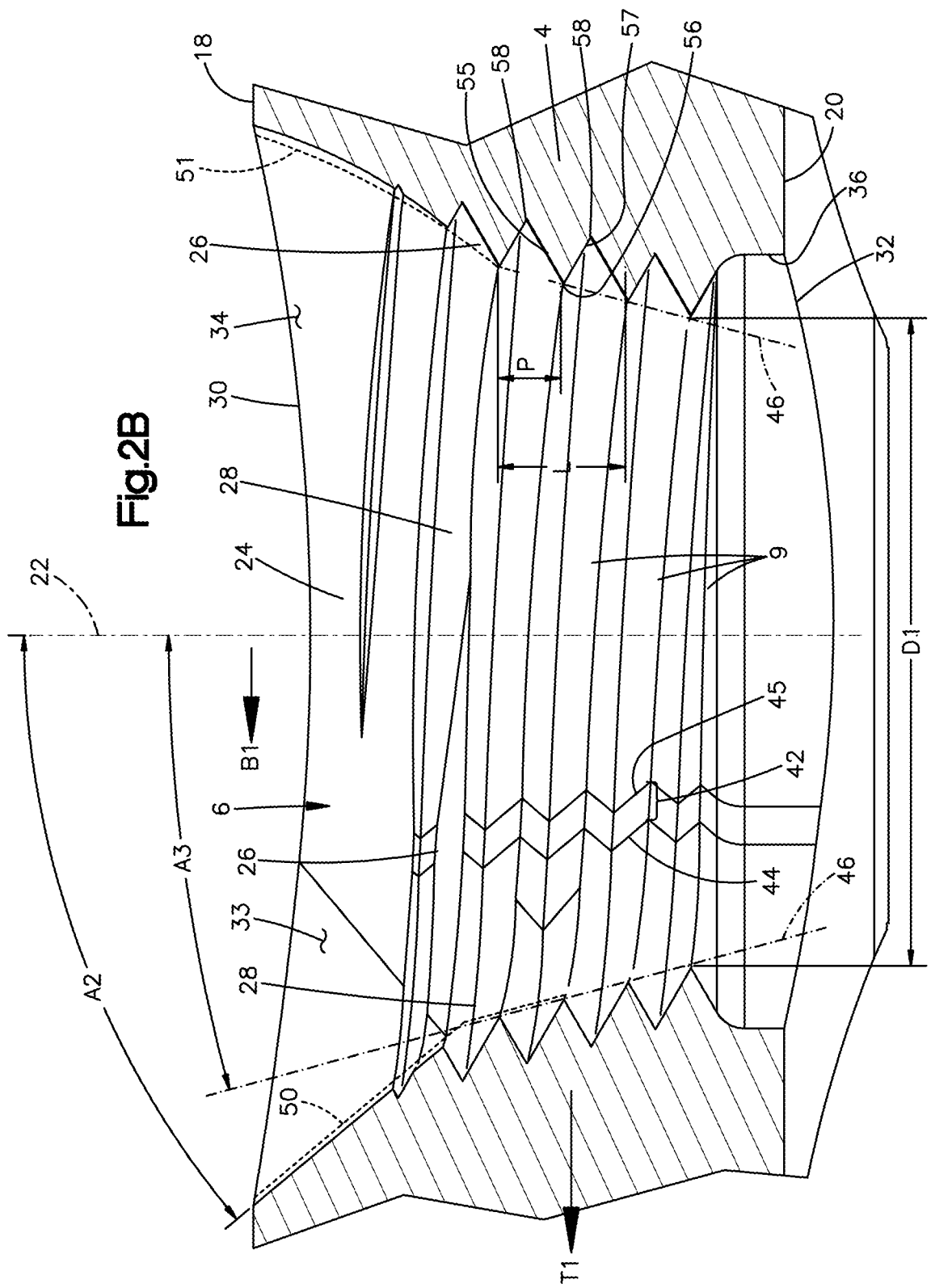
FIG. 2B is a sectional side view of the multi-use anchor hole taken along section line 2B-2B of FIG. 2A.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

The embodiments disclosed herein pertain to multi-use holes in a bone plate. In some of the embodiments disclosed herein, a multi-use hole includes (1) threaded locking structures for optional locking engagement with a threaded head of a locking bone anchor (e.g., a "locking bone screw") and (2) structure(s) for optional dynamic compression responsive to eccentric (axially offset) insertion of a head of a non-locking bone anchor (e.g., a "cortex screw" or "compression screw") within the hole. As used herein, the term "dynamic compression" refers to an act of engaging a bone anchor against a bone plate in a manner causing the bone plate to translate relative to the bone anchor and underlying patient anatomy along a direction that is generally perpendicular to an axis along which the bone anchor is inserted into underlying bone. Dynamic compression is particularly useful for moving fractured portions of bone relative to one another, such as for anatomical rejection to treat bone fractures. Such multi-use holes provide a physician with an option of using the hole for locking engagement with a locking bone anchor or for dynamic compression with a compression bone anchor.

The inventors have discovered, surprisingly and unexpectedly, that threaded locking holes having certain hole geometries can be alternatively used with compression bone anchors to achieve dynamic compression, even when contact between the anchor head and the interior plate surface within the hole occurs over or along the internal threads in the hole. Thus, threaded locking holes of the present disclosure, including portions of the holes having internal threads, can provide dynamic compression when the holes are used with compression anchors. In this manner, the multi-use holes of the present disclosure can provide selective locking engagement or dynamic compression without the need for a dedicated compression portion of the hole. Thus, the multi-use holes of the present disclosure provide significant advantages over combination holes (also referred to as "combi-holes") known in the art. One such advantage is that the multi-use holes of the present disclosure occupy less space of the plate by virtue of obviating the need for a dedicated compression portion of the hole. Thus, the bone plates described herein can include a higher hole quantity/density than prior art bone plates without sacrificing selective locking and compression functionality. Additionally, such higher hole density, combined with the option to use each hole for locking or for dynamic compression, provides enhanced patient-specific fracture fixation treatment, which provides further advantages in that such treatments can be less invasive and require a shorter healing and recovery period.

Referring to FIGS. 1A-1C, a bone plate 4 has a plate body 5 that defines therein one or more multi-use holes 6. As used herein, the term "multi-use hole" refers to a plate hole that is configured for selective use with either a compression bone anchor, such as a compression screw 7 (see FIGS. 3A-4B), or a locking bone anchor, such as a locking screw. The plate body 5 defines interior surfaces 24 that respectively define the holes 6. Within each multi-use hole 6, the interior surface 24 further defines one or more compression structures, such as ramp surfaces or "ramps" 33, and one or more locking structures, such as internal threads 9, within the hole 6. The internal threads 9 can also be referred to as "plate threads" or "hole threads." The compression structure(s) are configured to engage a head of a compression bone anchor 7, and the locking structures are configured to engage a head of a locking bone anchor. In the present embodiment, the multi-use holes 6 are particularly configured to translate the plate 4 substantially along a longitudinal direction X oriented along a longitudinal axis 3 of the plate 4. In other embodiments, one or more of the holes 6 can be configured to translate the plate 4 along a direction angularly offset from the longitudinal direction X.

The bone plate 4 can be a bridge plate, as shown, although other bone plate types and configurations are within the scope of the present disclosure. The plate body 5 is elongate along the longitudinal axis 3 and can define a first end 10 and a second end 12 spaced from each other along the longitudinal direction X. The plate body 5 can also define a first lateral side 14 and a second lateral side 16 spaced from each other along a lateral direction Y that is substantially perpendicular to the longitudinal direction X. The bone plate 4 can also define an upper plate surface 18 (also referred to herein as an "outer surface" 18) configured to face away from the bone and an opposed lower plate surface 20 (also referred to herein as a "bone-facing surface") configured to face the bone. The upper and lower plate surfaces 18, 20 are spaced from each other along a vertical direction Z substantially perpendicular to each of the longitudinal direction X and the lateral direction Y. It is to be appreciated that, as used herein, the terms "longitudinal", "longitudinally", and derivatives thereof refer to the longitudinal direction X; the terms "lateral", "laterally", and derivatives thereof refer to the lateral direction Y; and the terms "vertical", "vertically", and derivatives thereof refer to the vertical direction Z. It should also be appreciated that a plane that contains the longitudinal and laterals directions X, Y can be referred to herein as a "horizontal" plane X-Y.

The multi-use holes 6 extend from the upper plate surface 18 to the lower plate surface 20 along a central hole axis 22. The central hole axis 22 is oriented along an axial hole direction. As used herein, the term "axial direction" (e.g., "axial hole direction" and "axial screw direction") is defined as the direction along which the respective axis extends. Furthermore, the directional terms "axial", "axially", and derivatives thereof refer to the respective axial direction. Thus, as used herein, the directional term "axially upward" and derivatives thereof refers to the axial hole direction from the lower plate surface 20 toward the upper plate surface 18. Conversely, the term "axially downward" and derivatives thereof refers to the axial hole direction from the upper plate surface 18 toward the lower plate surface 20. Thus, "axially upward" and "axially downward" are each mono-directional components of the "axial direction", which is bi-directional. In the embodiments depicted in the Figures, the axial hole direction (and thus also the central hole axis 22) is oriented along the vertical direction Z. Accordingly, the axial hole direction is also denoted by "Z" throughout this disclosure. It should be appreciated, however, that the scope of the present disclosure covers embodiments in which the axial hole direction (and thus also the central hole axis 22) is offset from the vertical direction Z at an oblique angle. It should also be appreciated that when the terms "axially upper", "axially lower," and the like are used with reference to a compression screw 7 or locking screw, such terms refer to a central axis 52 of the screw, particularly as the screw would be oriented within the hole 6 (see FIGS. 3A-4B).

Referring now to FIG. 1C, the multi-use holes 6 can be arranged in the plate 4 in a manner providing the plate 4 with multi-directional compression. For example, the holes 6 can be arranged in a first group of holes 6 along a first longitudinal region 4a of the plate 4 and a second group of holes 6 along a second longitudinal region 4b of the plate 4. In this example, the first and second longitudinal regions 4a, 4b extend to a common boundary at a longitudinal midpoint XM of the plate 4, and each hole 6 of the first group is configured to provide dynamic compression (i.e., to translate the plate 4) in a first translation direction T1, such as a first longitudinal direction X1 along the longitudinal axis 3 toward the first end 10 of the plate 4, and each hole 6 of the second group is configured to provide dynamic compression in a second translation direction T2, such as a second longitudinal direction X2 opposite the first longitudinal direction X1. It should be appreciated that the arrangement of the multi-use holes 6 can be adapted as needed to provide the plate 4 with dynamic compression capabilities in various directions according to the needs of a particular surgical treatment.

Referring now to FIGS. 2A and 2B, within the multi-use hole 6, the interior surface 24 extends axially downward from an upper perimeter 30 of the hole 6 located at an interface with the upper plate surface 18 (FIG. 2A). The interior surface 24 can also define an undercut surface 36 (also referred to herein as a "relief surface") that extends axially upward from a lower perimeter 32 of the hole 6 which is located at an interface with the lower plate surface 20 (FIG. 2B). The locking structures of the hole 6 can be configured to provide variable-angle insertion of the locking bone anchor therein. For example, the locking structures can include columns 26 defined by the interior surface 24 within the hole 6. The columns 26 are sequentially located about a circumference of the interior surface 24. The interior surface 24 also defines a plurality of recesses 28 sequentially located circumferentially between the columns 26. Stated differently, the columns 26 and recesses 28 are alternately disposed along a circumference of the interior surface 24. The columns 26 and recesses 28 extend axially between the upper and lower plate surfaces 18, 20. The columns 26 and recesses 28 can be evenly spaced along the circumference of the hole 6. However, in other embodiments, the columns 26 and/or recesses 28 can be un-evenly spaced about the circumference of the hole 6. Each of the recesses 28 can define a central recess axis 37, each of which can be parallel with the central hole axis 22, although other orientations are possible for the central recess axes 37. Each central recess axis 37 can also be radially spaced from the central hole axis 22 by a distance R1. The plate threads 9 extend through the columns 26 and at least portions of the recesses 28 along one or more thread paths between the upper and lower plate surfaces 18, 20. Portions of the plate threads 9 that traverse a column 26 can be referred to herein as "column threads" 9.

As shown in FIG. 2A, each column 26 can define a first surface 42 substantially facing the central hole axis 22. The first surface 42 can also be referred to as an "innermost surface" of the column 26. Thus, the first surface 42 defines crests 56 of the column threads 9. The first surface 42 of each column 26 extends between a first side 44 and a circumferentially opposed second side 45 of the column 26. The first and second sides 44, 45 of each column 26 can define interfaces between the column 26 and the circumferentially adjacent recesses 28. The first surfaces 42 of the columns 26 can collectively define segments of a downward-tapering, generally frusto-conical shape, particularly one that defines a central cone axis coincident with the central hole axis 22.

The one or more thread paths can include a pair of non-intersecting thread paths (i.e., double-lead); however in other embodiments the one or more thread paths can include a single thread path (i.e., single-lead), or three or more thread paths (e.g., triple-lead, etc.). The thread paths are preferably helical, although other thread path types are within the scope of the present disclosure. As shown, the plate threads 9 can circumferentially traverse each of the columns 26 and recesses 28 in an uninterrupted fashion. In other embodiments, however, portions of the recesses 28 can circumferentially interrupt the plate threads 9 or, stated differently, the plate threads 9 can "bottom-out" along one or more and up all of the recesses 28.

The columns 26 are configured such that, during insertion of a locking screw within the hole 6, a screw shaft of the locking screw or compression screw bypasses the columns 26, such that the interior surface 24 within the hole 6 engages a head of the compression screw or locking screw. In the latter case, after the screw shaft bypasses the columns 26, the plate threads 9 in turn engage external threads on the head of the locking screw in a manner providing locking engagement between the locking screw and the bone plate 4. The structure and operation of the columns 26 is more fully described in U.S. Pat. No. 10,772,665, issued Sep. 15, 2020, in the name of Bosshard et al. ("the '665 Reference"); U.S. Patent Publication No. 2019/0328430 A1, published Oct. 31, 2019, in the name of Bosshard et al. ("the '430 Reference"); U.S. patent application Ser. No. 16/437,105, filed Jun. 11, 2019, in the name of Oberli et al. ("the '105 Reference"); and U.S. patent application Ser. No. 17/062,708, filed Oct. 5, 2020, in the name of Oberli et al. ("the '708 Reference"), the entire disclosures of each of which are hereby incorporated by reference herein. The aforementioned references are appended herewith at Appendices 1 (the '665 Reference); 2 (the '430 Reference); 3 (the '105 Reference); and 4 (the '708 Reference), and are each included as part of the present disclosure.

Referring again to FIG. 2A, the multi-use hole 6 defines a hole shape or "profile" in a horizontal reference plane X-Y. The hole 6 shape can thus be referred to as a "horizontal hole profile". In the present embodiment, at least an axial portion of the hole 6 has a generally polygonal horizontal hole profile. In particular, the hole 6 of the present embodiment has a trigon (i.e., generally triangular) horizontal profile, although in other embodiments the hole 6 can have other types of polygonal horizontal profiles (e.g., rectangle, pentagon, hexagon, etc.), or can have a circular horizontal profile, as discussed in more detail below. The hole 6 can have a first column 26a, a second column 26b, and a third column 26c located in a clockwise sequence along the circumference of the interior surface 24. The first column 26a of the present embodiment is aligned with the longitudinal axis 3. The hole 6 also has a first recess 28a opposite the first column 26a, a second recess 28b opposite the second column 26b, and a third recess 28c opposite the third column 26c. The plate threads 9 can extend along a thread path that corresponds to the horizontal profile of the hole 6. Moreover, other features defined by the interior surface 24 can have a corresponding polygonal (e.g., trigon) horizontal profile, including the upper perimeter 30 and the neutral lead in surface(s) 34 (at least those portions thereof separate from the compression ramp 33), the one or more undercut surfaces 36, and the lower perimeter 32.

In the illustrated embodiment, the first surfaces 42 of the columns 26 have linear horizontal profiles. In other embodiments, one or more of the first surfaces 42 can have arcuate profiles having a relatively large radii (as measured from the central hole axis 22). Each column 26 can define a column centerline 43 that is spaced equidistantly between the first and second sides 44, 45 of the column 26. In a horizontal reference plane X-Y, the hole 6 can define a main radius R2 measured from the central hole axis 22 to the first surface 42 of the column 26 at the column centerline 43.

In the present embodiment, the recesses 28 extend tangentially from the first and second sides 44, 45 of the associated columns 26. In this manner, the first surfaces 42 of the columns 26 effectively define the sides of the trigon, while the recesses 28 effectively define the corners of the trigon, each as viewed in the horizontal reference plane. Accordingly, the columns 26 and recesses 28 of the present embodiment can also be referred to respectively as "sides" and "corners" 28 of the trigon-shaped hole 6. Each of the corners 28 can define a corner radius R3, measured from the corner axis 37. The plate threads 9 extend along respective splines that revolve about the central hole axis 22 helically along the trigon profile of the interior surface 24 between the upper plate surface 18 and the lower plate surface 20. Additionally, the interior surface 24, including the columns 26 as well as the corners 28, tapers inwardly toward the central hole axis 22 from the upper plate surface 18 toward the lower plate surface 20. Moreover, as shown, the plate threads 9 can circumferentially traverse the columns 26 and the corners 28 in an uninterrupted fashion (i.e., the plate threads 9 need not bottom-out in the corners 28). Accordingly, the plate threads 9 can transition smoothly and continuously between the columns 26 and the corners 28.

The first surfaces 42 of each column 26 define a column length LC measured between the sides 44, 45 of the column 26. In the present embodiment, the column length LC can be substantially consistent within each column 26 as the thread path advances between the upper and lower surfaces 18, 20 of the plate 4. In such embodiments, the column length LC can also be referred to as a "side length" LC of the trigon-shaped hole 6. The columns 26 of the present embodiment can have substantially equivalent column lengths LC, thus providing the hole 6 with a substantially equilateral triangular shape, as shown. Alternatively, the column lengths LC of two or all of the columns can differ from one another, as described in more detail below. In further embodiments, the column length LC of one or more and up to all of the columns 26 can successively increase as the thread path advances from the upper surface 18 toward the lower surface 20 of the plate 4, thereby causing the corner radii R3 to progressively decrease toward the lower surface 20 of the plate 4.

Referring again to FIGS. 2A and 2B, the one or more compression structures of the multi-use hole 6 can include at least one lead-in surface 33 or "compression ramp" 33 that tapers axially downward from the upper perimeter 30 toward the lower plate surface 20. Each compression ramp 33 is configured to cause the plate 4 to translate in a specific translation direction T1 in the horizontal plane X-Y responsive to engagement with the head of a compression bone anchor 7. In the present embodiment, the hole 6 includes a compression ramp 33 that extends less than a full revolution about the central hole axis 22. For example, the ramp 33 can be located on a specific side of the hole 6 in the intended translation direction T1. Stated differently, the translation direction T1 extends substantially horizontally from the central hole axis 22 toward the ramp 33.

As shown in FIG. 2A, the compression ramp 33 is centrally located along the longitudinal axis 3, such that the ramp 33 is configured to direct or "funnel" or otherwise influence the translation direction T1 to be along the longitudinal direction X. For example, the compression ramp 33 can define a crescent shape as viewed in a horizontal reference plane X-Y, such that a maximum horizontal dimension L0 of the crescent occurs along the longitudinal axis 3. The ramp 33 can revolve about the central hole axis 22 from a first terminus 35 to a second terminus 35. In this manner, the ramp 33 can define an angular ramp span A1 measured between the termini 35 in a horizontal plane X-Y. As shown, the ramp 33 can revolve about the central hole axis 22 such that one or both of the termini 35 is located across the column centerline 43 of the adjacent column 26. In other embodiments, however, the compression ramp 33 can have an angular span A1 such that one or both of the termini 35 is located respectively on a near side of the column centerline 43 of the adjacent column 26. Stated differently, the first compression ramp 33 need not extend across one or both of the adjacent column centerlines 43. It should be appreciated that in further embodiments, any and up to each of the corners 28 can include a compression ramp 33 for directing dynamic compression responsive to eccentric insertion of a compression screw 27 toward the respective corner 28. Such compression ramps 33 can be separate from one another or can be defined by different portions of a single ramp surface.

The angular ramp span A1 can be in a range of about 10 degrees up to about 360 degrees, and more particularly from about 40 degrees 180 degrees, and more particularly from about 120 degrees to about 160 degrees. The hole 6 can also include a neutral lead-in surface 34 that extends from the upper perimeter 30 axially downward into the hole 6 and revolve about the central hole axis 22 and can extend to interfaces with the compression ramp 33.

Referring now to FIG. 2B, the compression ramp 33 tapers axially downward from the upper perimeter 30 and can be intersected by the plate threads 9. In the present embodiment, the compression ramp 33 has a linear surface profile in a reference plane that extends along the central hole axis 22 and the longitudinal direction X. This reference plane is also referred to herein as an "axial reference plane." The ramp 33 is oriented at an acute ramp angle A2 with respect to the central hole axis 22. The ramp angle A2 can be in a range of about 0.5 degrees to about 85 degrees, and more particularly in a range of about 30 degrees to about 60 degrees, and more particularly in a range of about 42 degrees to about 48 degrees. It should be appreciated that, in other embodiments, the compression ramp 33 can have a concave arcuate profile in the axial reference plane. In such embodiments, the ramp angle A2 can be measured between the central hole axis 22 and a tangent axis that intersects the compression ramp 33 at a location thereof in the axial reference plane.

In the illustrated embodiment, the compression ramp 33 extends from the upper perimeter 30 to, and is intersected by, the threads 9. In other embodiments, a portion of the neutral lead-in surface 34 can extend axially downward from the compression ramp 33, such as at the first recess 28a. In this manner, the compression ramp 33 can define a first compression ramp 33, and such portion of the neutral lead-in surface 34 can define a second, axially lower compression ramp, such as along the first corner 28a. In such an embodiment, the second compression ramp 34 can extend axially downward from the first compression ramp 33 to the plate threads 9. The first ramp 33 defines a first ramp angle A2, and the second compression ramp 34 can define a second ramp angle, which can be less than (i.e., steeper than) or greater than (i.e., shallower than) the first ramp angle A2 with respect to the central hole axis 22 in an axial reference plane along the longitudinal axis 3.

Referring again to FIG. 2B, the plate threads 9 have a cross-sectional profile in the axial reference plane. Such as cross-sectional profile is also referred to as a "thread-form," and includes crests 56, roots 58, and upper and lower flanks 55, 57 that extend between the crests 56 and roots 58. As used herein with reference to the plate threads 9, the term "crest" refers to the apex of a fully-developed thread-form. The thread-forms of the plate threads 9 are configured for complimentary engagement (i.e., intermeshing) with exterior threads on the head of a locking screw, particularly for providing favorable mating engagement therebetween. The thread-forms of the plate threads 9 are also configured to engage an outer surface on the head of a compression screw inserted eccentrically within the hole 6. In this manner, the plate threads 9 can be characterized as defining a compression ramp for providing dynamic compression. It should be appreciated that, in this manner, the compression ramp 33 and the plate threads 9 together can provide complimentary dynamic compression.

The crests 56 of the plate threads 9 can be sharp, although one or more and up to all of the crests 56 can be rounded for reducing stress concentrations and also for reducing undesirable mechanical interference with the exterior threads on the head of the locking screw. In other embodiments, one or more of the crests 56 can be truncated and can have a linear crest profile, as described in more detail below.

In the reference plane, the crests 56 of the plate threads 9 extend along a crest trajectory axis 46. In the present embodiment, the crest trajectory axis 46 is linear, and can be oriented at an acute crest trajectory angle A3 relative to the central hole axis 22. The crest trajectory angle A3 can be in a range of about 5 degrees to about 30 degrees, and more particularly in a range of about 10 degrees to about 20 degrees, and preferably in a range of about 13 degrees to about 17 degrees. As shown, the crest trajectory angle A3 can be less (i.e., steeper) than the ramp angle A2, although in other embodiments the crest trajectory angle A3 can be equivalent to or greater (i.e., shallower) than the ramp angle A2. In yet other embodiments, one or both of the compression ramp 33 and the crest trajectory axis 46 can be curvilinear, such that various portions of the crest trajectory axis 46 can be shallower, equivalent to, and/or steeper than various portions of the compression ramp 33, and vice versa. The crest trajectory angle A3 is configured, among other things, to prevent the head of a locking screw or compression screw from passing completely through the multi-use hole 6.

The threads 9 can also define a thread pitch P that extends between axially adjacent crests 56 along the axial direction, and is in a range of about 0.05 mm to about 5.0 mm. The plate threads 9 also define a thread lead L, which can also be defined at the crests 56, and can be in a range of 0.05 mm to about 5.00 mm. The thread pitch P and thread lead L can be as more fully described in the '105 and '708 References. The hole 6 can define a minimum minor diameter D1, which can be measured at the axially lowermost crest 56 along the crest trajectory axis 46. The undercut surface 36 can truncate at least a portion of one or more of the plate threads 9. The undercut surface 36 can extend circumferentially continuously and uninterrupted along a full revolution about the central hole axis 22. Alternatively, the undercut surface 36 can be circumferentially interrupted by one or more of the corners 28.

It should be appreciated that the plate threads 9 described herein are configured to enhance the mechanical strength of a locked thread interface between the plate threads 9 and the exterior threads on the head of a locking screw, and also to be sufficiently robust to provide dynamic compression responsive to engagement with the head 27 of a compression screw 7.

With continued reference to FIG. 2B, the interior surface 24 defines at least one contact profile 50 in the axial reference plane that extends along the translation direction T1. Each contact profile 50 can be characterized as a path along which the head 27 of the compression anchor 7 (FIGS. 3A-4B) contacts the interior surface 24 within the hole 6 as the head 27 advances axially downward within the hole 6 along the central axis 52 of the compression anchor 7 that is eccentric with respect to the central hole axis 22, meaning that the central screw axis 52 is offset from the central hole axis 22 in an offset direction during insertion. It should be appreciated that the central screw axis 52 can also be referred to as the "insertion axis" 52 along which the screw is inserted through the hole 6. The geometry of each contact profile 50 can be tailored to enhance the translation of the bone plate 4 in the respective translation direction during eccentric head 27 insertion within the hole 6. In the present embodiment, the compression ramp 33 is intersected by the threads 9, which are therefore part of the compression structures within the hole 6. Accordingly, the interior surface 24 of the present embodiment can define a first contact profile 50 that is defined at least by the compression ramp 33 and is also partially defined by the plate threads 9. In this manner, portions of the threads 9, such as the crests 56, can also define a compression ramp within the hole 6. In the present embodiment, the compression structures are configured such that a first offset direction B1 is in the same axial reference plane as the first contact profile 50.

Referring now to FIGS. 3A and 3B, methods of using the multi-use hole 6 of the present embodiment in a bone plating operation for selective dynamic compression will now be described, according to an example technique of eccentrically inserting a compression screw 7 toward the associated corner 28 and compression ramp 33 aligned with the first translation direction T1. During the bone plating operation, a physician can insert a shaft 25 of a compression screw 7 through the hole 6 along an insertion axis 52 and drive the shaft 25 into underlying bone, such as a bone segment 100. In this example, the physician can cause the insertion axis 52 to be offset from the central hole axis 22 by a first offset distance O1 measured in the first offset direction B1 toward the corner 28 and the compression ramp 33. In this example, the first offset direction B1 is in the first translation direction T1. As shown in FIG. 3A, the physician can further drive the shaft 25 through the hole 6 along the insertion axis 52 at the first offset distance O1 in a manner causing an outer surface 74 of the head 27 of the compression screw 7 to engage the interior surface 24 of the hole 6 at a first position of the screw head 27 with respect to the interior surface 24. At the first position, the outer surface 74 of the screw head 27 contacts the interior surface 24 at a first initial contact location 75, such as along the contact profile 50, such as on the compression ramp 33. It should be appreciated that a maximum of the first offset distance O1 can be determined by a variety of factors, such as the corner radius R3, the minimum minor diameter D1 of the plate threads 9, and the major diameter of a threaded shaft 25 of the compression screw 7, such that the threads of the threaded shaft 25 can bypass the plate threads 9 during insertion along the insertion axis 52 toward the corner 28.

As shown in FIG. 3B, after the outer surface 74 of the head 27 contacts the interior surface 24 at the first initial contact location 75 (FIG. 3A), the physician can further drive the compression screw 7 axially downward along the insertion axis 52, causing the outer surface 74 of the head 27 to travel or ride along the interior surface 24, such as along the first contact profile 50 (FIG. 2B), to a second position of the screw head 27 relative to the interior surface 24, which can be a fully seated position of the screw head 27 within the hole 6. The interfacing geometries of the interior surface 24 of the hole 6, such as along the contact profile 50, and the outer surface 74 of the head 27, causes the plate 4 and the underlying bone segment 100 to translate in the first translation direction T1 as the outer surface 74 rides along the interior surface 24, as the screw head 27 advances axially downward along the insertion axis 52. In this manner, the bone segment 100 can translate in the translation direction T1 in a manner reducing a gap G (FIG. 3A) between the bone segment 100 and an adjacent bone segment 102.

In the present embodiment, the size and shape of the screw head 27 is configured such that the screw axis 52 will be substantially co-extensive with the central hole axis 22 when the screw head 27 is fully seated within the hole 6, as shown. In such embodiments, the first offset distance O1 effectively defines a first translation distance L1 of the plate 4 (along the first translation direction T1) provided by the eccentric screw insertion. The trigon shape of the hole 6 in the present embodiment can cause the outer surface 74 of the screw head 27 to contact the columns 26 and be remote from the corners 28, including the contact profile 50, when fully seated in the hole 6.

The multi-use holes 6 of the present disclosure are versatile in that the side of the hole 6 opposite the compression ramp 33 can also be used to achieve dynamic compression, which occurs in a second translation direction T2 opposite first translation direction T1. Referring now to FIGS. 4A and 4B, methods of using the multi-use hole 6 of the present embodiment for selective dynamic compression in the second translation direction T2 will now be described, according to an example technique of eccentrically inserting the compression screw 7 toward the associated column 26 opposite the compression ramp 33 along the second translation direction T2. In this example, the physician can insert the shaft 25 of the compression screw 7 through the hole 6 an into an underlying bone segment 100 along an insertion axis 52 that is offset from the central hole axis 22 by a second offset distance O2 measured in a second offset direction B2 toward the column 26. In this example, the second offset direction B2 is in the second translation direction T2. As shown in FIG. 4A, the physician inserts the shaft 25 through the hole 6 along the insertion axis 52 at the second offset distance O2 in a manner causing the outer surface 74 of the head 27 to engage the interior surface 24 of the hole 6 at a third position of the screw head 27 relative to the interior surface 24. At the third position, the outer surface 74 of the screw head 27 contacts the interior surface 24 at a second initial contact location 77, which can occur at an interface between the upper perimeter 30 and the neutral lead-in surface 34. As with eccentric insertion of the screw 7 toward the compression ramp 33 (FIGS. 3A and 3B), the maximum second offset distance O2 can be determined by minimum minor diameter D1 of the plate threads 9 and the major diameter of a threaded shaft 25 of the compression screw 7, such that the threads of the threaded shaft 25 can bypass the plate threads 9 during insertion along the insertion axis 52. However, because geometry of the corners 28 provides that first surfaces 42 of the columns 26 are closer to the central hole axis 22 that the interior surface 24 along the corners 28, the maximum second offset distance O2 is shorter than offset distance O1 in the present embodiment of the hole 6.

As shown in FIG. 4B, after the outer surface 74 of the head 27 contacts the interior surface 24 at the second initial contact location 77, the physician can further drive the compression screw 7 axially downward along the insertion axis 52 into the underlying bone segment 100, causing the outer surface 74 of the head 27 to travel or ride along the neutral lead-in surface 34 and the column 26, and optionally along a portion of the plate threads 9 of the column 26, to a fourth position of the screw head 27 relative to the interior surface 24. The fourth position can be the fully seated position of the screw head 27 within the hole 6, and thus can be equivalent to the second position (see FIG. 3B). In this manner, the neutral lead-in surface 34, the column, and a portion of the threads 9 thereof can define a second contact profile 51 (see FIG. 2B) in the axial reference plane. The interfacing geometries of the outer surface 74 of the screw head 27 and the interior surface 24 of the hole 6, such as along the second contact profile 51, causes the plate 4 and the bone segment 100 to translate in the second translation direction T2 as the outer surface 74 rides along the interior surface 24, optionally until the screw head 27 is fully seated within the hole 6, at which position the screw axis 52 is substantially co-extensive with the central hole axis 22. In such embodiments, the second offset distance O2 effectively defines a second translation distance L2 of the plate 4 along the second translation direction T2. Because the maximum first offset distance O1 is greater than the maximum second offset distance O2 in the present embodiment, the maximum first translation distance T1 is greater than the maximum second translation distance T2.

It should be appreciated that the configuration of the hole 6 according to the present embodiment provides numerous additional options for dynamic compression along other translation directions. For example, the physician can elect to translate the plate 4 in a third translation direction T3 by inserting the compression screw 7 eccentrically toward the second corner 28b or in a fourth translation direction T4 by inserting the compression screw 7 eccentrically toward the third corner 28c.

Referring to FIGS. 5A-5C, in other embodiments the bone plate 4 can employ multi-use holes 6 that have multiple compression ramps, such as a first ramp 33a and a second ramp 33b opposite each other along the longitudinal axis 3. As in the embodiment described above (FIGS. 2A-2B), first ramp 33a can be centered along the longitudinal axis 3 at the first corner 28a. The second ramp 33b can centered along the longitudinal axis 3 at the first column 26a, and can otherwise be a substantial mirror image of the first ramp 33a. Accordingly, like the first ramp 33a, the second ramp 33b can be configured to direct, funnel, or otherwise influence the second translation direction T2 to be along the longitudinal direction X. In the present embodiment, the neutral lead-in surface 34 can extend from the upper perimeter 30 axially downward into the hole 6 and revolve about the central hole axis 22 and can extend to interfaces with the first and second compression ramps 33a, 33b.

Figure 6A:
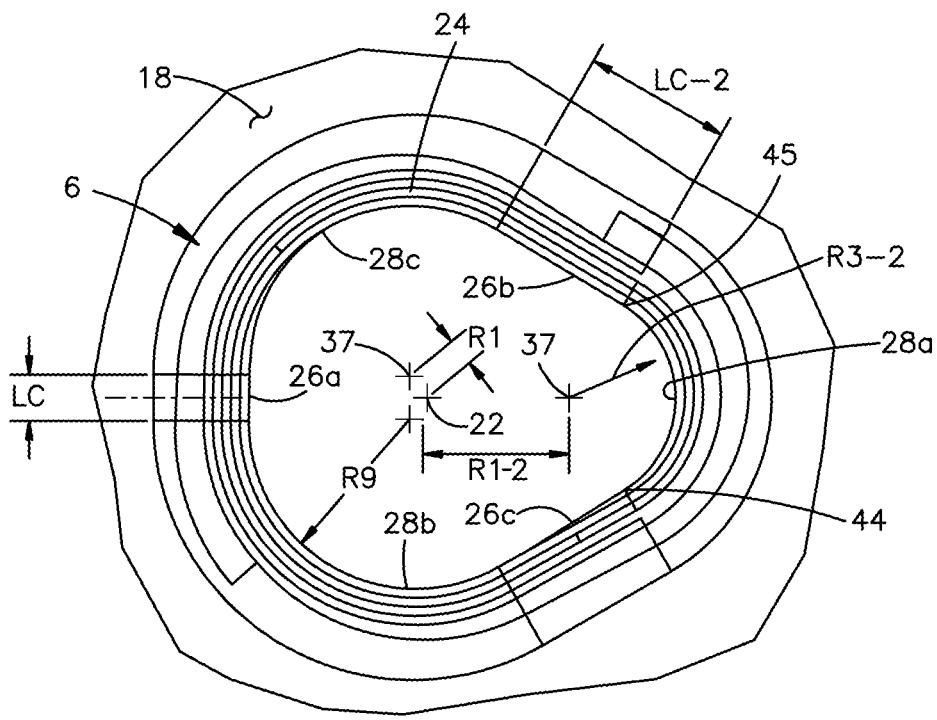
FIGS. 6A and 6B are top views of a multi-use anchor hole that is elongated along a direction perpendicular to a central axis of the hole, according to an additional embodiment of the present disclosure.
Figure 6B:
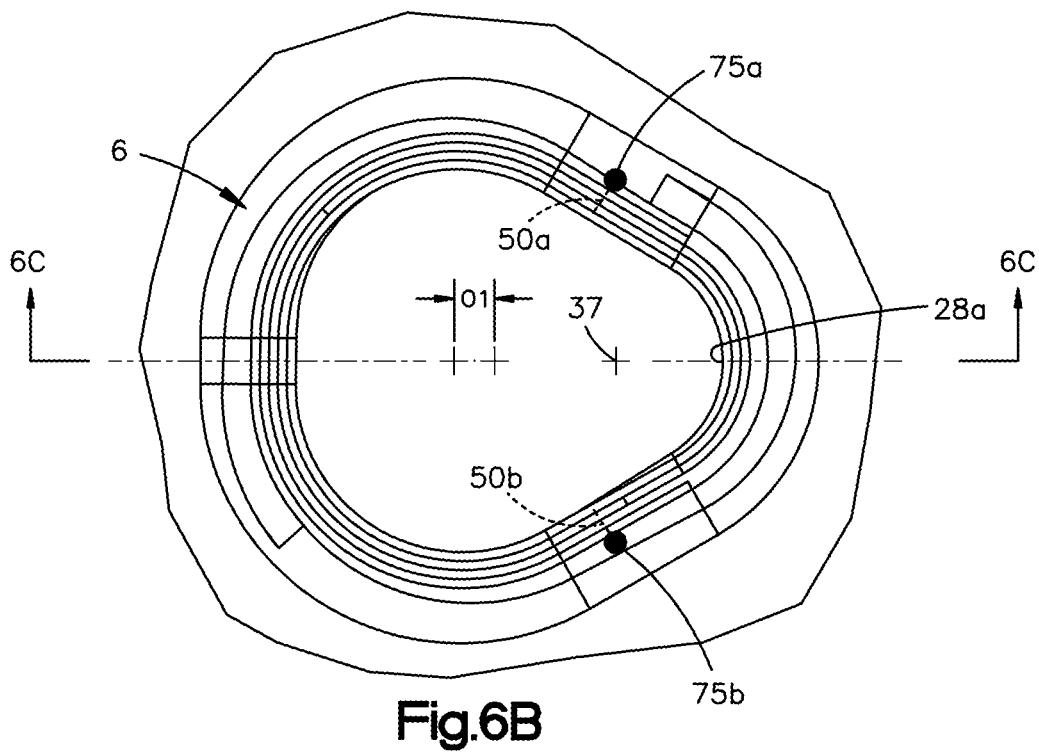

Referring to FIGS. 6A-6D, in additional embodiments, the shape of the hole 6 can be further adapted to provide an increased translation distance L1. As shown in FIGS. 6A and 6B, the second and third columns 26b, 26c of the present embodiment can define column lengths LC-2 that are greater than a length LC of the first column 26a, thereby causing the hole 6 to be elongated in the horizontal reference plane X-Y, particularly along the first translation direction T1. In this embodiment, the corner axis 37 of the first corner 28a can be spaced from the central hole axis 22 at a distance R1-2 that is greater than distances R1 by which the corner axes 37 of the second and third corners 28b, 28c are spaced from the central hole axis 22. The first corner 28a can have a corner radius R3-2 shorter than the corner radii R3 of the second and third corners 28b, 28c. The foregoing adjustments to the hole 6 geometry can effectively provide additional space between the central hole axis 22 and the first corner 28a for eccentric insertion of the compression screw 7 for increased dynamic compression. Stated differently, the hole 6 of the present embodiment can provide a greater maximum offset distance O1 and translation distance L1 (FIG. 6D) compared to the embodiments described above.

As shown in FIGS. 6B and 6C, the physician can insert the compression screw 7 eccentrically within the hole 6 such that the insertion axis 52 is offset in the first offset direction B1 toward the first corner 28a, such as along a longitudinal axis 3' that intersects the column centerline 43 of the first column 26a. In this example, the first offset direction B1 is in the first translation direction T1. As shown in FIG. 6B, at such an offset the outer surface 74 of the head 27 of the compression screw 7 can engage the interior surface 24 of the hole 6 at a first position of the screw head 27 relative to the interior surface 24. At the first position, the outer surface 74 of the screw head 27 contacts the interior surface 24 at first and second initial contact locations 75a, 75b, which can be offset from the longitudinal axis 3'. As shown, the first and second initial contact locations 75a, 75b can be on the second and third columns 26b, 26c. Thus, in the present embodiment, the screw head 27 can travel along at least two contact profiles that 50a, 50b (FIG. 6B) that are opposite each other with respect to the longitudinal axis 3'. Thus, the second and third columns 26b, 26c can define corresponding compression ramps.

As shown in FIGS. 6B and 6D, after the outer surface 74 of the head 27 contacts the interior surface 24 at the first and second initial contact locations 75a, 75b, the physician can further drive the compression screw 7 axially downward along the insertion axis 52, causing the outer surface 74 of the head 27 to travel or ride along the interior surface 24, such as along the contact profiles 50a, 50b, from the first position to a second position of the screw head 27 relative to the interior surface 24. In this embodiment, the interior surface 24 of the hole 6 can be characterized as providing a pair of compression rails, along which the outer surface 74 of the screw head 27 can travel during plate translation along the translation direction T1 to the first translation distance L1, until the screw head 27 reaches the second position, which can be the fully seated position of the screw head 27 within the hole 6. As in the embodiments described above, the screw axis 52 can be substantially co-extensive with the central hole axis 22 when the screw head 27 is fully seated within the hole 6. Also as above, the first offset distance O1 can effectively define the first translation distance L1. It should be appreciated that, in the present embodiment, dynamic compression via eccentric screw insertion toward the first column 26a can be substantially similar to that described above with reference to FIGS. 4A and 4B.

Figure 7A:
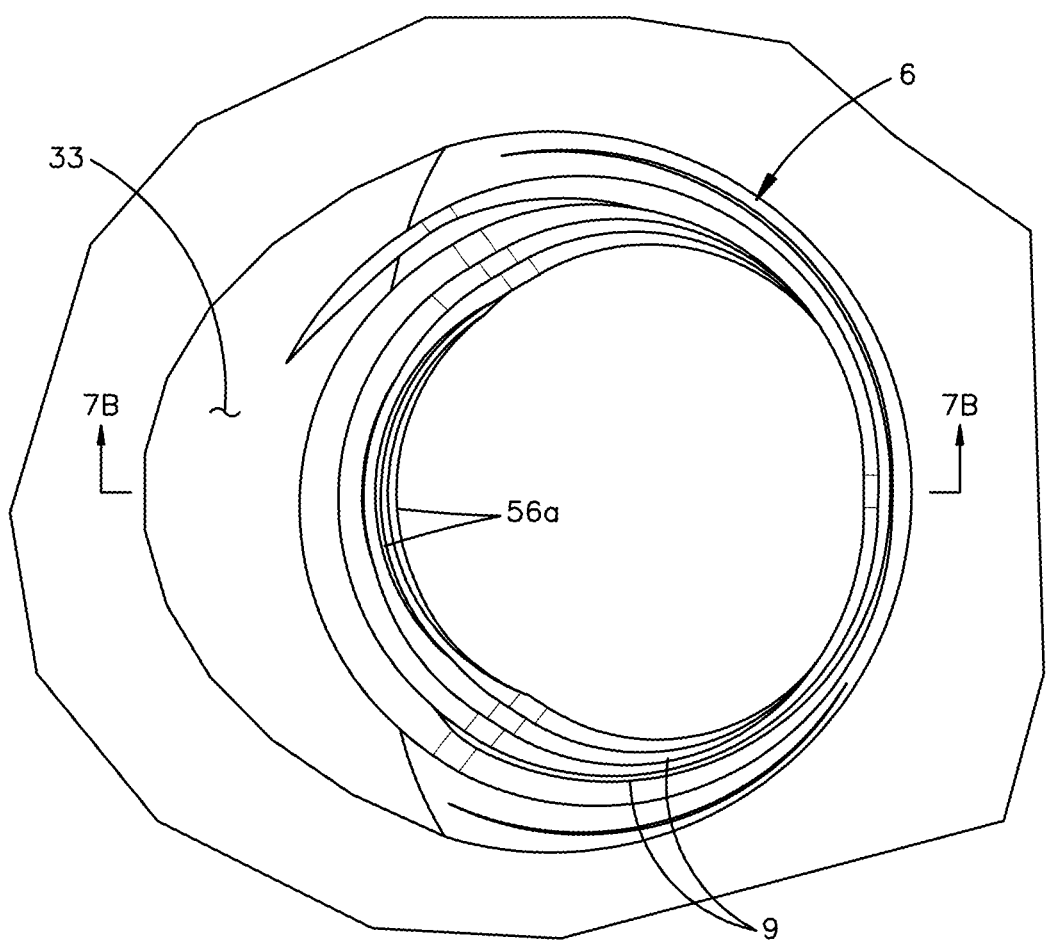
FIG. 7A is a perspective view of a multi-use anchor hole having truncated crests adjacent a bottom of the hole, according to yet another embodiment of the present disclosure.
Figure 7B:
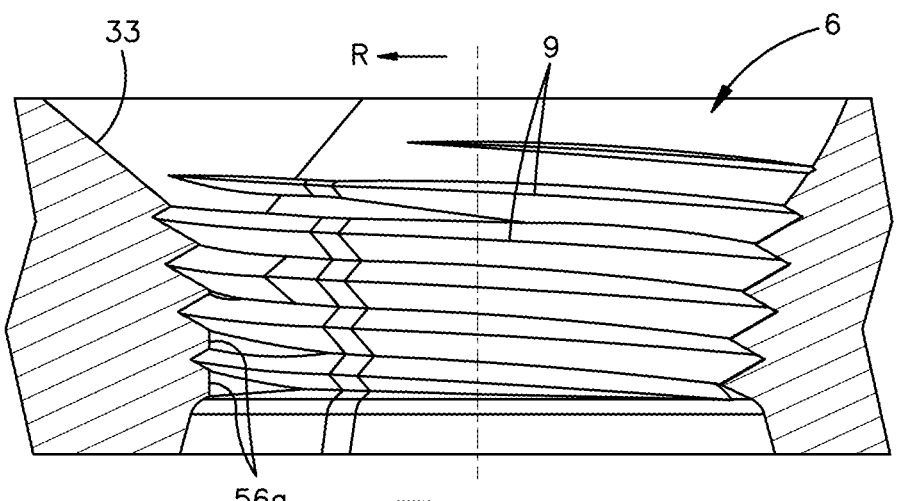
FIG. 7B is a sectional side view of the multi-use anchor hole taken along section line 7B-7B of FIG. 7A.

Referring now to FIGS. 7A and 7B, in additional embodiments of a multi-use hole 6, one or more of the plate threads 9 adjacent the axial lower portion of the hole 6 can be truncated, such as by having truncated crests 56a, in a manner providing additional clearance along the radial direction R for the threads of the threaded shaft 25 of the compression screw 7 during eccentric insertion toward the compression ramp 33.

As described above, the multi-use hole 6 can have a circular hole shape in a horizontal reference plane. Examples of such circular holes 6 are shown in FIGS. 8A-9B. The plate threads 9 of the circular multi-use holes 6 can extend along respective splines that revolve about the central hole axis 22 helically along the circular profile of the interior surface 24 of the hole 6.

As shown in FIGS. 8A and 8B, a circular multi-use hole 6 can include a compression ramp 33 located on a specific side of the hole 6, such as in an intended translation direction T1 from the central hole axis 22. For example, the compression ramp 33 can be centrally located along the longitudinal axis 3, similar to the manner described above with reference to FIG. 2A. The ramp 33 can be configured to direct, funnel, or otherwise influence dynamic compression along the translation direction T1.

As shown in FIG. 9A and 9B, a circular multi-use hole 6 can have multiple compression ramps, such as a first ramp 33a and a second ramp 33b opposite each other along the longitudinal axis 3. The first and second ramps 33a, 33b can each be centered along the longitudinal axis 3 and can be substantial mirror images of each other, as in the embodiment described above with reference to FIGS. 5B and 5C. The first and second compression ramps 33a, 33b can be configured to direct, funnel, or otherwise influence dynamic compression along respective first and second translation directions T1, T2 extending from the central hole axis 22. The circular multi-use holes 6 can be employed for dynamic compression in various other translation directions responsive to eccentric screw insertion. For example, circular holes 6 can provide dynamic compression along virtually any translation direction extending radially outward from the central hole axis 22 to the location of eccentric screw insertion within the hole 6.

It should be appreciated that although the illustrated embodiments of the present disclosure show the multi-use holes 6 as having a minimum minor thread diameter less than a maximum diameter of the head 27 of the compression screw 7, the holes 6 and/or compression screws 7 of the present disclosure can be adapted such that a compression screw 7 can engage the interior surface 24 within a hole 6 in a manner providing dynamic compression even should the minimum minor thread diameter of the hole 6 be greater, even significantly greater, than the maximum diameter of the head 27 of the compression screw 7.

The plate body 5, compression screws 7, and locking screws described herein can each comprise one or more biocompatible materials. By way of non-limiting examples, the plate body 5 can be formed of a material selected from a group comprising: metal, such as titanium, titanium alloys (e.g., titanium-aluminum-niobium (TAN) alloys, such as Ti-6Al-7Nb, and titanium-aluminum-vanadium (TAV) alloys such as Ti-6Al-4V, titanium molybdenum alloys (Ti—Mo) or any other molybdenum metal alloy, and nickel-titanium alloys, such as nitinol), stainless steel, and cobalt base alloys (e.g., cobalt-chrome alloys); composite materials; polymeric materials; ceramic materials; and/or resorbable materials, including resorbable versions of the foregoing material categories (metals, composites, polymers, ceramics). Also by way of non-limiting examples, the compression screws 7 and locking screws can be formed of a material selected from a group comprising: metal, such as titanium, titanium alloys (e.g., TAN alloys, TAV alloys, such as Ti-6Al-4V, titanium molybdenum alloys (Ti—Mo) or any other molybdenum metal alloy, and nickel-titanium alloys, such as nitinol), stainless steel, cobalt base alloys (e.g., cobalt-chrome alloys); composite materials; polymeric materials; ceramic materials; and/or resorbable materials, including resorbable versions of the foregoing material categories (metals, composites, polymers, ceramics). Preferably, the material of the compression screws 7 and locking screw ha a hardness that is greater than that of the material of the plate body 5. This parameter contributes to the threaded locking characteristics and the dynamic compression characteristics described throughout the present disclosure. Preferably, the plate body 5 primarily or entirely comprises titanium and the compression screws 7 and locking screws primarily or entirely comprise TAN. It should be appreciated, however, that other material compositions of the bone plates 4 and/or the screws are within the scope of the present disclosure.

Moreover, surfaces of the plate body 5 and/or the screws can optionally be subjected to one or more processes, such as coating, treating, and/or finishing processes, which can be performed to provide such surfaces, or the underlying subject body material, with certain characteristics, such as to adjust hardness, softness, and/or friction parameters of the body material, as more fully described in the '105 and '708 References.

It should be appreciated that the various hole 6 parameters described above are provided as exemplary features for adapting the holes 6 to achieve selective dynamic compression or locking engagement with the heads of respective compression screws and locking screws. These parameters can be adjusted as needed without departing from the scope of the present disclosure.

It should also be appreciated that in additional embodiments, the interior surface 24 of any multi-use hole 6 can be defined by an insert plate body (e.g., an "insert" or "inlay") that is fitted within an axial aperture or receptacle of the plate body 5. In such embodiments, the bone plate 4 can be provided in a kit that includes a plurality of interchangeable inserts having different hole 6 shapes and geometries, such that the physician can select the particular insert having the desired dynamic compression characteristics needed.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. In particular, one or more of the features from the foregoing embodiments can be employed in other embodiments herein. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone plate, comprising:
an outer surface and a bone-facing surface opposite the outer surface; and an interior surface that defines a hole that extends from the outer surface to the bone-facing surface along a central hole axis, wherein the interior surface further defines:
  a first ramp extending from the outer surface toward the bone-facing surface;
  plate threads extending from the first ramp toward the bone-facing surface, wherein the plate threads are configured for optional locking engagement with external threads on a first head of a locking bone fixation member;
  a contact profile defined at least by the first ramp in a reference plane that extends along the central hole axis, wherein the contact profile is spaced from the central hole axis in an offset direction perpendicular to the central hole axis, and the contact profile is configured to translate the bone plate in the offset direction responsive to contact with an exterior surface of a second head of a compression bone fixation member as the second head advances within the hole along an insertion axis that is offset from the central hole axis in the offset direction; and
  a second ramp in the contact profile, wherein the second ramp is located between the first ramp and the bone-facing surface,
  wherein the plate threads define crests, roots, and flanks that extend from associated ones of the roots to associated ones of the crests, and the contact profile is further defined by at least some of the crests, wherein the at least some of the crests are rounded in the reference plane.

2. The bone plate of claim 1, wherein the first ramp is oriented at an acute angle with respect to the central hole axis, and the acute angle is in a range from about 30 degrees to about 80 degrees.

3. The bone plate of claim 1, wherein the plate threads intersect at least a portion of the first ramp.

4. The bone plate of claim 1, wherein the first ramp is oriented at a first ramp angle with respect to the central hole axis, the second ramp is oriented at a second ramp angle with respect to the central hole axis, and the second ramp angle is less than the first ramp angle.

5. The bone plate of claim 1, wherein the interior surface also defines a relief surface extending from the plate threads to the bone-facing surface, and at least some of the plate threads adjacent the relief surface are truncated.

6. The bone plate of claim 1, wherein the hole has a polygonal hole profile in a second reference plane that is orthogonal to the central hole axis.

7. The bone plate of claim 6, wherein the interior surface defines a plurality of columns and a plurality of recesses alternately disposed along a circumference of the hole, and the offset direction extends from the central hole axis toward one of the recesses.

8. The bone plate of claim 1, wherein the contact profile is a first contact profile, the offset direction is a first offset direction, the interior surface defines a second contact profile spaced from the central hole axis in a second offset direction that is angularly offset from the first offset direction, and the second contact profile is configured to translate the bone plate in a translation direction offset from the first offset direction responsive to contact with the exterior surface of the second head as the second head advances along the insertion axis when the insertion axis is offset from the central hole axis in the second offset direction.

9. The bone plate of claim 8, wherein the translation direction is in the second offset direction, and the second offset direction is opposite the first offset direction, and the first and second offset direction are oriented along a longitudinal axis of the bone plate.

10. A bone plate, comprising
  an outer surface and a bone-facing surface opposite the outer surface; and
  an interior surface that defines a hole that extends from the outer surface to the bone-facing surface along a central hole axis, wherein the interior surface further defines:
    a ramp extending from the outer surface toward the bone-facing surface;
    plate threads extending from the ramp toward the bone-facing surface, wherein the plate threads are configured for optional locking engagement with external threads on a first head of a locking bone fixation member,
    a contact profile defined at least by the ramp in a reference plane that extends along the central hole axis, wherein the contact profile is spaced from the central hole axis in an offset direction perpendicular to the central hole axis, and the contact profile is configured to translate the bone plate in the offset direction responsive to contact with an exterior surface of a second head of a compression bone fixation member as the second head advances within the hole along an insertion axis that is offset from the central hole axis in the offset direction,
  wherein the plate threads define crests, roots, and flanks that extend from associated ones of the roots to associated ones of the crests, and the contact profile is further defined by at least some of the crests,
  wherein the hole has a trigonal hole profile in a second reference plane that is orthogonal to the central hole axis, the trigonal hole profile being defined by three sides of the interior surface and three corners of the interior surface, wherein each corner of the three corners extends between adjacent ones of the three sides.

11. The bone plate of claim 10, wherein the offset direction extends from the central hole axis toward one of the corners.

12. The bone plate of claim 10, wherein the three sides have respective straight profiles as viewed in respective reference planes parallel with the reference plane.

13. A method of seating a bone screw in a hole defined by an interior surface of a bone plate, comprising:
  inserting a shaft of the bone screw through the hole and into underlying bone, wherein the shaft is inserted through the hole at an offset distance measured between a central axis of the bone screw and a central axis of the hole along a first direction that is perpendicular to the central axis of the hole;
  contacting an outer surface of a head of the bone screw against at least one ramp surface defined by the interior surface within the hole, wherein the interior surface includes internal threads that extend between the at least one ramp surface and the underlying bone; and
  driving the bone screw, during the contacting step, toward the underlying bone along the central axis of the screw, thereby translating the bone plate in the first direction relative to the bone screw,
  wherein the hole has a trigon shape in a reference plane orthogonal to the central axis of the hole, the trigon shape being defined by three sides of the interior surface and three corners of the interior surface, wherein each corner of the three corners extends between adjacent ones of the three sides.

14. The method of claim 13, wherein the inserting step comprises positioning the central axis of the bone screw between the central axis of the hole and a first corner of the three corners, wherein a longitudinal axis of the bone plate intersects the first corner such that the first direction is along the longitudinal axis.

15. The method of claim 14, wherein the at least one ramp revolves about the central axis of the hole along the first corner, such that the at least one ramp is centered along the longitudinal axis.

16. The method of claim 13, wherein the inserting step comprises positioning the central axis of the bone screw between the central axis of the hole and a first side of the three sides, wherein a longitudinal axis of the bone plate intersects the first side such that the first direction is along the longitudinal axis.

17. The method of claim 13, wherein the driving step engages the outer surface of the head of the bone screw against one or more of the internal threads.

18. The method of claim 13, wherein the underlying bone is a first bone segment, and translating the bone plate in the first direction relative to the bone screw reduces a gap between the first bone segment and a second bone segment.

* * * * *